United States Patent
Werp et al.

[11] Patent Number: 6,152,933
[45] Date of Patent: Nov. 28, 2000

[54] INTRACRANIAL BOLT AND METHOD OF PLACING AND USING AN INTRACRANIAL BOLT TO POSITION A MEDICAL DEVICE

[75] Inventors: Peter R. Werp, St. Louis; Walter M. Blume, Webster Groves, both of Mo.; William Penny, Arden Hills, Minn.; Michael A. Lawson, Ballwin, Mich.

[73] Assignee: Stereotaxis, Inc., St. Louis, Mo.

[21] Appl. No.: 09/189,645

[22] Filed: Nov. 10, 1998

Related U.S. Application Data

[60] Provisional application No. 60/065,108, Nov. 12, 1997.

[51] Int. Cl.[7] .......................... A61B 17/00; A61M 29/00
[52] U.S. Cl. ............................................. 606/130; 604/165
[58] Field of Search ................................ 606/1, 130, 184, 606/185; 604/164, 167, 169, 256, 165

[56] References Cited

U.S. PATENT DOCUMENTS

| | | | |
|---|---|---|---|
| 3,021,842 | 2/1962 | Flood | 606/130 |
| 3,460,537 | 8/1969 | Zeis | 606/130 |
| 4,244,362 | 1/1981 | Anderson . | |
| 4,445,501 | 5/1984 | Bresler . | |
| 4,809,694 | 3/1989 | Ferrara | 606/130 |
| 5,176,697 | 1/1993 | Hasson et al. . | |
| 5,354,270 | 10/1994 | Wilk et al. . | |
| 5,360,417 | 11/1994 | Gravener et al. . | |
| 5,389,080 | 2/1995 | Yoon . | |
| 5,415,617 | 5/1995 | Kraus . | |
| 5,425,382 | 6/1995 | Golden et al. . | |
| 5,445,615 | 8/1995 | Yoon . | |
| 5,454,179 | 10/1995 | Bulka . | |
| 5,484,420 | 1/1996 | Russo . | |
| 5,622,169 | 4/1997 | Golden et al. . | |
| 5,662,600 | 9/1997 | Watson et al. . | |
| 5,713,858 | 2/1998 | Heruth et al. . | |
| 5,713,869 | 2/1998 | Morejon . | |
| 5,728,103 | 3/1998 | Picha et al. . | |
| 5,879,368 | 3/1999 | Hoskin et al. | 606/185 |

*Primary Examiner*—Michael Buiz
*Assistant Examiner*—William Lewis
*Attorney, Agent, or Firm*—Howell & Haferkamp, L.C.

[57] ABSTRACT

An intracranial bolt, for installation in an opening in the skull to provide access to the brain for a medical device, has a bore therethrough for the passage of the medical device, and an inflatable member in the bore which when inflated engages a medical device in the bore, releasably anchoring the device. The inflatable member comprises a cylinder of flexible sheet material inside the bore and secured to the wall of the bore defining an annular pocket therebetween. A passage extends through the bolt to the pocket for the introduction of fluid into the pocket to expanding radially inwardly. The bolt in a medical procedure on the brain by forming an opening in the skull; installing the intracranial bolt in the opening in the skull; and securing the cap on the bolt. When it is time to conduct the procedure, the cap is removed and a medical device can be inserted into the brain through the bolt. The inflatable member can be inflated to temporarily hold the medical device in place.

28 Claims, 4 Drawing Sheets

INTRACRANIAL BOLT AND METHOD OF PLACING AND USING AN INTRACRANIAL BOLT TO POSITION A MEDICAL DEVICE

This appln. claims the benefit of U.S. Provisional No. 60/065,108 filed Nov. 12, 1997.

FIELD OF THE INVENTION

This invention relates to an intracranial bolt for placement in an opening in the skull to provide access to the brain, and to a method of placing and using the intracranial bolt to position a medical device in the brain.

BACKGROUND OF THE INVENTION

There are instances where it is desirable to have a sterile access to the brain for conducting a diagnostic or therapeutic procedure in a non-sterile environment. For example, techniques have been developed to position medical devices in the brain using an externally applied magnetic field. These techniques are most conveniently employed in a non-sterile environment where the equipment is available for generating the appropriate magnetic field. Similarly, it is often desirable to monitor a procedure with x-ray or magnetic resonance imaging equipment that is available only in non-sterile environments. There are also situations where repeated access to the brain is needed to complete a diagnostic or therapeutic procedure, but it is undesirable to perform repeated surgeries each time access is required.

It is also desirable to be able to releasably anchor medical devices inserted in to the body to prevent unintentional movement during a medical procedure, or to allow a medical device to remain in place between medical procedures, rather than reinserting the medical device at the start of each procedure.

SUMMARY OF THE INVENTION

The intracranial bolt of the present invention can be placed in an opening in the skull to provide access to the brain. The intracranial bolt has a proximal end and a distal end adapted for placement in an opening in the skull, and a bore extending between the proximal end and the distal end for the passage of a medical device. A removable cap can be provided for the proximal end of the bolt to close the proximal end of the bore.

In the preferred embodiment of the invention, there is an inflatable member in the bore which, when inflated, engages a medical device in the bore releasably anchoring the device within the bore. In the manner the intracranial bolt functions like a clamp, releasably securing a medical device without damaging it. The inflatable member preferably comprises a flexible liner in the bore, that defines a pocket between the liner and bore, and a passage through the bolt to the pocket for filling the pocket with a fluid to urge the liner radially inwardly to constrict this bore and engage a medical device therein.

According to the method of this invention, the intracranial bolt can be placed in the skull in a sterile environment, such as a procedure or an operating room. An opening is made in the skull, and the distal end of the intracranial bolt is placed in the opening. A removable cap can be secured over the proximal end to close the proximal end of the bore. Thus sealed, the patient can then be moved out of the sterile environment of the procedure or operating room, to other locations, for example where there is magnetic field generating equipment for positioning medical devices introduced through the intracranial bolt, or where there is x-ray or magnetic resonance imaging equipment for monitoring a procedure being conducted with medical devices extending through the intracranial bolt.

With the intracranial bolt of the preferred embodiment, once a medical device has been properly placed through the bolt and into the brain, the device can be secured, either during the procedure, or between procedures, by inflating the inflatable member in the bore. The intracranial bolt prevents undesired movement of the device during the procedure, and/or undesired movement of the device between procedures. This allows, for example, a catheter to be placed through the intracranial bolt and positioned into the brain and held in place for guiding diagnostic or therapeutic devices to a particular location in the brain. When it is desired to move or remove the catheter or other medical device, the inflatable member can be partially or fully deflated.

For procedures where repeated access is required, a medical device can be held in place in the bore, and the proximal end of the intracranial bolt can be closed with the cap. The medical device remains securely in place, anchored by the inflatable member, until the procedure is continued.

Thus the intracranial bolt of the present invention provides convenient access to the brain for diagnostic and therapeutic procedures. After installation, the bolt provides controlled sterile access, even in non-sterile environments, allowing the use of specialized equipment that is not practically available in a sterile operating room. The intracranial bolt is capable of securely temporarily anchoring a medial device extending through it during and between procedures, but does not damage the medical device. These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
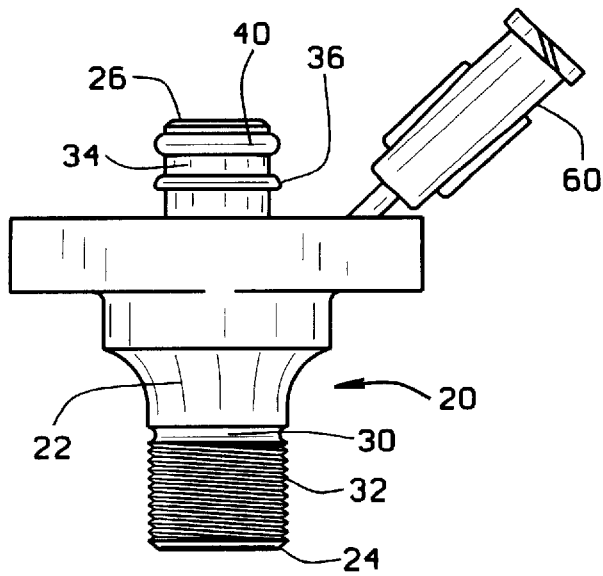
FIG. 1 is an elevational view of an intracranial bolt constructed according to the principles of this invention.
Figure 2:
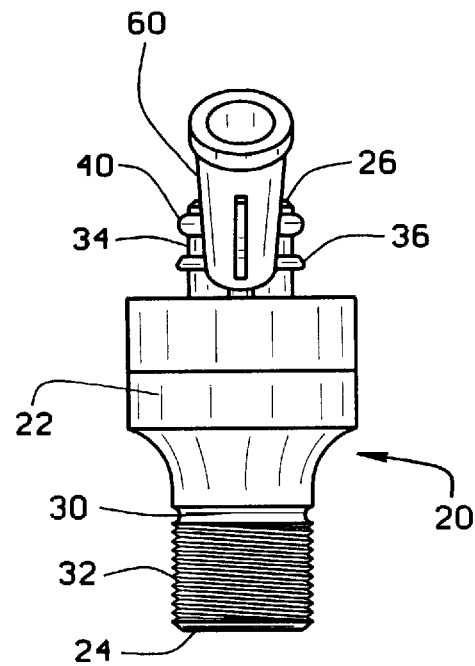
FIG. 2 is an elevational view of the intracranial bolt taken from the right side as shown in FIG. 1.
Figure 3:
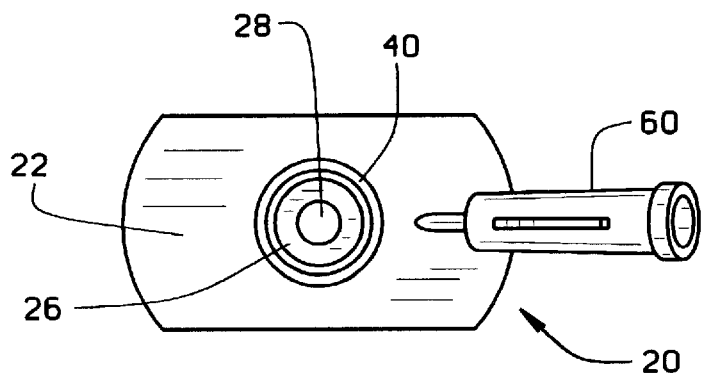
FIG. 3 is a front plan view of the intracranial bolt.
Figure 4:
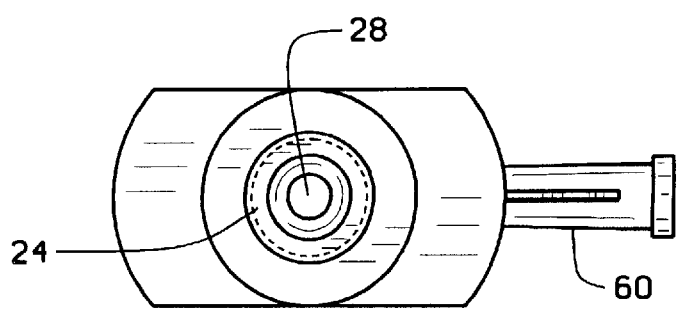
FIG. 4 is a rear plan view of the intracranial bolt.
Figure 5:
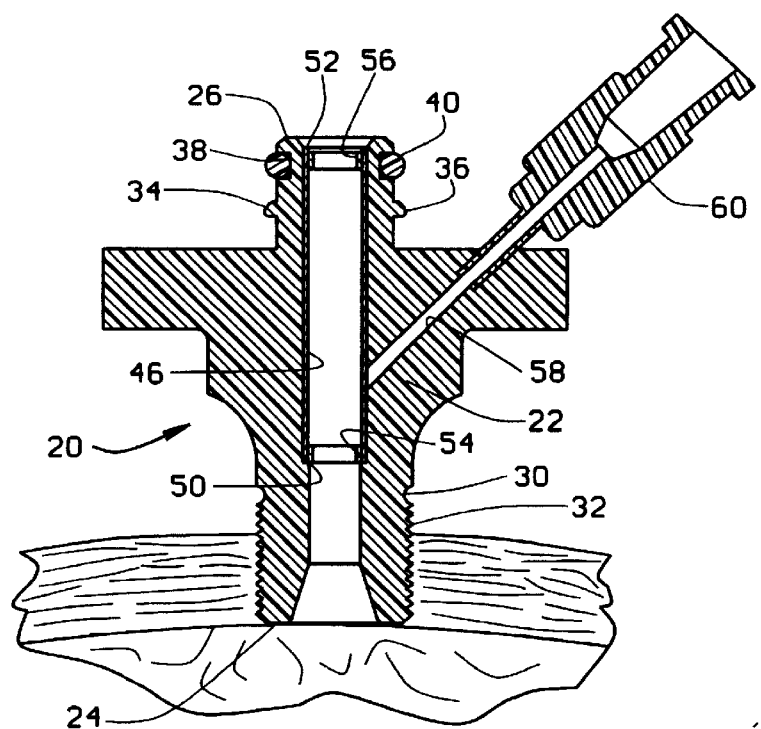
FIG. 5 is an enlarged cross-sectional view of the intracranial bolt, shown as it would be placed in an opening in a skull.

An intracranial bolt constructed according to the principles of the present invention is indicated generally as 20 in the figures. The intracranial bolt 20 is adapted to be secured in an opening in the skull. The intracranial bolt 20 comprises a body 22 having a front or distal end 24 (see FIG. 4) and a rear or proximal end 26, with a bore 28 extending through the body between the proximal and distal ends. The body 22 is preferably made of a plastic material such as polycarbonate, that is not affected by magnetic fields, and is transparent to x-ray and magnetic imaging techniques.

The front or distal end 24 of the body 22 has a generally cylindrical extension 30, with external threads 32 for securing the intracranial bolt in a burr hole formed in the skull. The rear or proximal end 26 of the body 22 has a generally cylindrical stem 34, having a raised circumferential lip 36 thereon, and a circumferential groove 38 therein for mounting a resilient o-ring 40. The o-ring 40 seals with, and the lip 36 helps secure, a removable cap 42 for closing the proximal end of the bore 28.

The cap preferably includes a socket 43 for mounting a marker 45. The marker 45 is preferably a hollow body that can be filled with a substance, such as vitamin e, that is opaque (but non-distorting) to magnetic resonance imaging. The marker provides a clear indication of the location and orientation of the intracranial bolt, which is otherwise transparent to magnetic resonance imaging, so that in a preprocedure magnetic resonance image, the path of the medical instrument through the intracranial bolt and into the brain can be planned in advance.

Figure 6A:
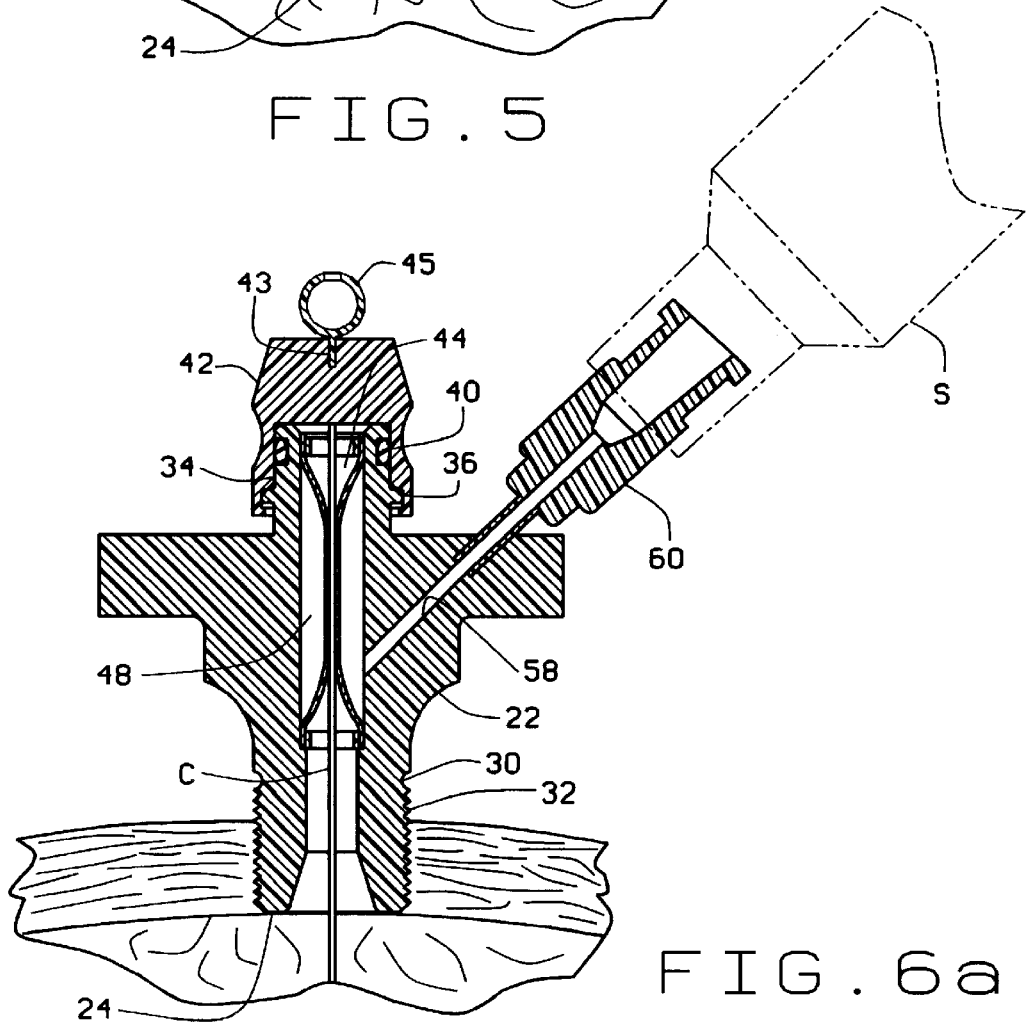
FIG. 6a is an enlarged cross-sectional view of the intracranial bolt, shown with the inflatable member inflated to secure a medical device in the bore of the intracranial bolt.

There is preferably an inflatable member 44 in the bore 28 which, when inflated, engages and secures a medical device extending through the bore as shown in FIG. 6a. In the preferred embodiment, the inflatable member 44 comprises a flexible panel 46 lining at least a portion of the bore 28, and forming a pocket 48 therebetween, and more preferably the flexible panel is cylindrical, lining the entire circumference of the bore 28 for at least a portion of its length. The first and second edges 50 and 52 of the flexible panel are secured to the wall of the bore 28 with adhesive. Rings 54 and 56 can be placed in the bore to further secure the edges of the panel against the wall of the bore.

Figure 6B:
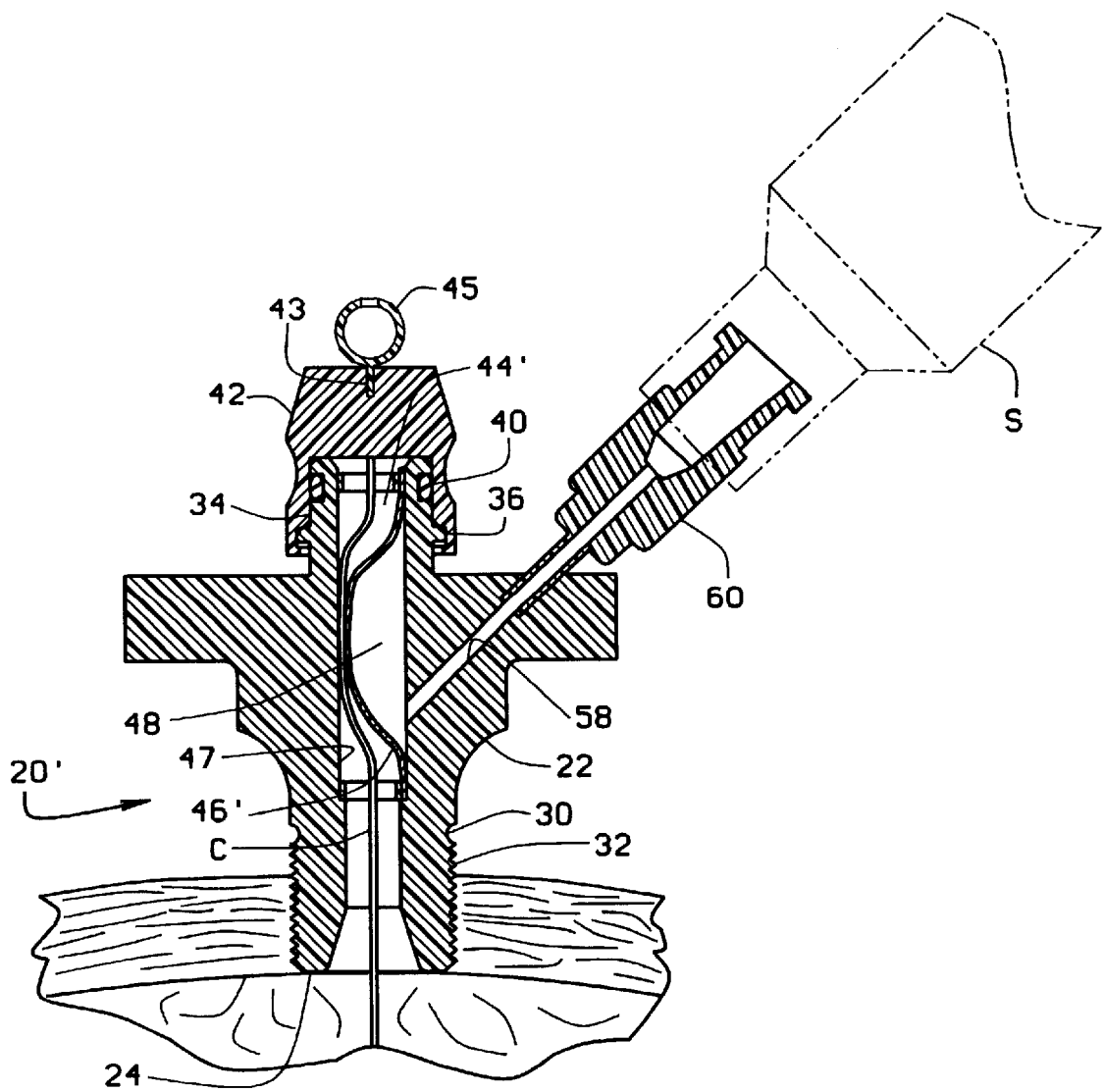
FIG. 6b is an enlarged cross-sectional view of a second embodiment of the intracranial bolt, shown with the inflatable member inflated to secure a medical device in the bore of the intracranial bolt.

A second embodiment of an intracranial bolt is indicated generally as 20' in FIG. 6b. Intracranial bolt 20' is similar in construction to intracranial bolt 20, and corresponding parts are identified with corresponding reference numerals. However, unlike intracranial bolt 20', in which the inflatable member 44 surrounds the medical device, engaging it between opposing portions, in intracranial bolt 20', the inflatable member 44', when inflated, engages and secures a medical device extending through the bore against an opposing wall 47 of the bore 28 as shown in FIG. 6b. In this second preferred embodiment, the inflatable member 44' comprises a flexible panel 46' lining at least a portion of the bore 28, and forming a pocket 48 therein. The flexible panel lines a part of the circumference of the bore 28 for at least a portion of its length. The first and second edges 50 and 52 of the flexible panel are secured to the wall of the bore 28 with adhesive. Rings 54 and 56 can be placed in the bore to further secure the edges of the panel against the wall of the bore.

A passage 58 extends through the body 22 to the pocket 48 formed between the wall of the bore 28 and the panel 46. A syringe fitting 60 is attached to the end of the passage 58. The fitting 60 is adapted to receive a syringe S (FIG. 6) so that fluid can be injected into the pocket 48 to urge the panel 46 radially inwardly into the bore 28 to engage a medical device, such as a catheter C, extending through the bore. The inflatable member 44 preferably engages the medical device with sufficient force to prevent unintentional movement of the device, thereby functioning as an anchor or clamp.

OPERATION

In operation, an incision is made in the scalp to expose the skull, and a burr hole is made in the skull. The intracranial bolt 20 is installed in the burr hole by threading the threads 32 into the burr hole. The bore 28 through the intracranial bolt provides access to the interior of the skull. After the intracranial bolt 20 is secured in the burr hole, the cap 42 can be secured on the stem 34, thereby sealing the bore 28 (and the access to the interior of the skull). The installation of the intracranial bolt is preferably done in a sterile environment, such as a procedure or an operating room, but after the intracranial bolt is installed, it can provide sterile access to the interior of the skull in any environment. More specifically, after installation of the intracranial bolt 20 the patient can be moved to another site, for example an x-ray or magnetic resonance imaging facility, or a site equipped with magnetic field generating equipment for introducing and guiding magnetic medical devices inside the skull. It is impractical to have such equipment in a sterile operating room environment, but the intracranial bolt provides sterile access to the interior of the skull for conducting medical procedures using such equipment in a non-sterile environment.

The intracranial bolt 20 can remain in place to provide repeated access during a course of treatment. Moreover, the intracranial bolt 20 can clamp or anchor medical devices both during and between medical procedures. For example in a diagnostic or therapeutic procedure it might be desirable to introduce a catheter into the skull. The catheter can pass easily into the skull through the bore 28 of the intracranial bolt 20. Once the catheter is in its desired position, the inflatable member 44 can be inflated to secure the catheter in the bore. More specifically, a syringe S can be mounted onto fitting 60 and inject fluid, such as air or saline solution, into the pocket 48 between the liner 46 and the wall of the bore 28. The fluid urges the liner 46 radially inwardly to engage the catheter C (or other medical device) in the bore 28, securing the catheter against inadvertent movement as shown in FIG. 6a. In the second preferred embodiment shown in FIG. 6b, the fluid urges the liner 46' inwardly and toward the opposing wall 47 of the bore 28, pressing the catheter against the opposing wall and preventing inadvertent movement.

The catheter C can be held in place, and the intracranial bolt 20 capped with cap 42 so that the catheter can be used for repeated access to the interior of the skull. For example, the catheter could be used as an access for taking biopsies, and left in place pending testing of the biopsies, for the administration of therapy. Alternatively, a course of therapy might require repeated delivery of medications to the same area, and the catheter can be held in place during the course of treatment.

Figure 7:
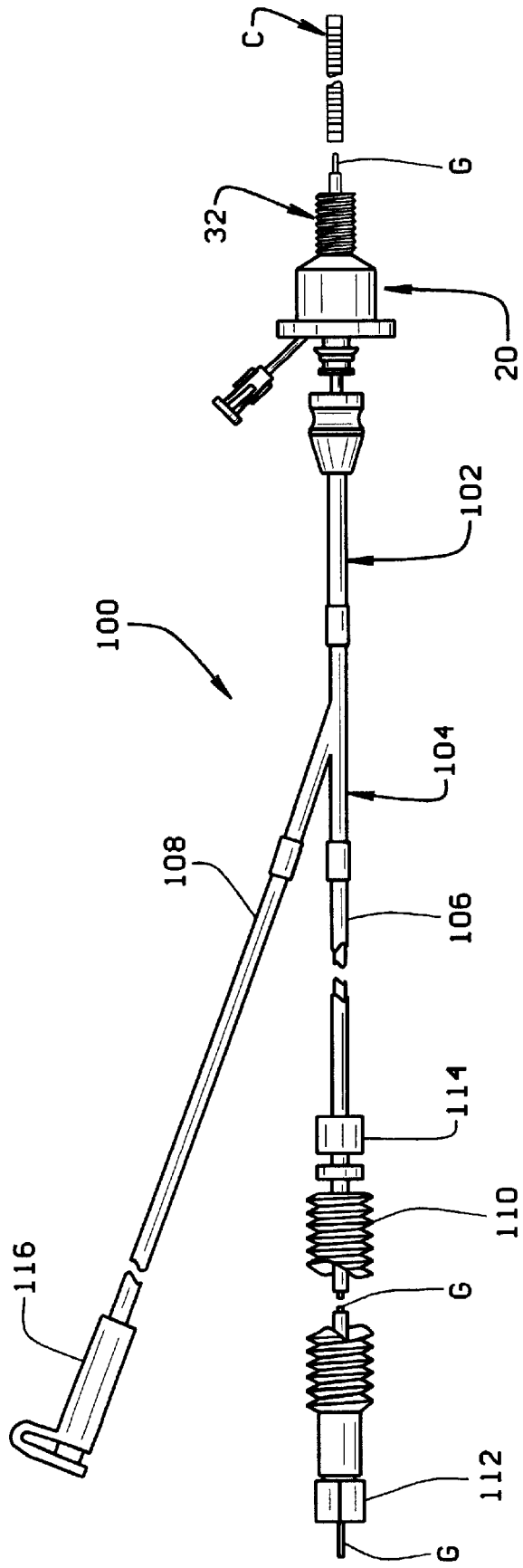
FIG. 7 is a schematic view of a catheter system that could be used with the intracranial bolt.

As shown in FIG. 7, the intracranial bolt 20 is conveniently used with the catheter system 100. An outer sheath 102 is secured to the intracranial bolt 20. The outer sheath 102 contains a "Y" 104 that splits the outer sheath into first and second branches 106 and 108. At the end of the first branch 106 of the outer sheath 102 is an expandable sheath 110. The expandable sheath 110 clamps over a guide wire G, and allows the movement of the guide wire in the outer sheath 102. The expandable sheath 110 comprises proximal and distal connectors 112 and 114, which are secured in a motor-driven mechanical drive system under the surgeon's control. The drive system advances the proximal connector 112 while holding the distal connector 114 stationary to move the guide wire. A catheter C is mounted over the distal end of the guide wire G, and is advanced through the intracranial bolt 20 with the advancement of the guide wire.

The second branch 108 terminates in an access port 116. After the catheter C is properly positioned, the intracranial bolt is operated to secure the catheter, and with the catheter secured, the guide wire can withdrawn past the "Y" 104. The access port 116 is opened, and an medical device, for example a biopsy tool, can be introduced through the branch 108 and into the catheter C, and through the catheter C into the brain.

Thus the intracranial bolt of the present invention provides sterile access to the interior of the skull, even in non sterile environments. Furthermore, in the preferred embodiment, the intracranial bolt can secure medical devices in place, during and/or between medical procedures.

What is claimed:

1. A clamp for releasably anchoring a medical device extending through an opening in a skull, the clamp comprising:
    a body adapted to be secured in the opening in the skull, the body having a bore therethrough for the passage of a medical device, and an inflatable member, positioned in the bore, which when inflated can engage a medical device passing through bore, to releasably anchor the medical device.

2. The clamp of claim 1 wherein the body is shaped to abut substantially a entire circumference of the opening, and the bore extends through the body and is itself surrounded by the body.

3. The clamp according to claim 1 wherein the inflatable member comprises a panel of flexible sheet material secured to the wall of the bore, and wherein there is a passage through the body, opening in the wall of the bore underneath the panel for introducing a fluid under the panel to cause the panel to extend into the bore.

4. The clamp according to claim 3 wherein the panel is generally cylindrical.

5. The clamp according to claim 1 wherein the inflatable member engages the medical device between opposing portions of the inflatable member.

6. The clamp according to claim 1 wherein the inflatable member engages the medical device against a wall of the bore.

7. A clamp for releasably anchoring a medical device extending through an opening in a skull, the clamp comprising:
    a body adapted to be secured in the opening in the skull, the body having a bore therethrough for the passage of a medical device; a panel of flexible sheet material secured to a wall of the bore to form a pocket between the panel and the wall, and a passage through the body communicating with the pocket; the panel expanding radially inwardly into the bore upon the introduction of fluid into the pocket to engage a medical device passing through the bore to releasably anchor the medical device.

8. The clamp of claim 7 wherein the body is shaped to abut substantially the entire circumference of the opening, and the bore extends through the body and is itself surrounded by the body.

9. The clamp according to claim 8 wherein the panel is generally cylindrical, having first and second ends, and wherein the panel is secured to the wall of the bore adjacent its first and second ends.

10. A clamp for installation in a bore in a skull to releasably anchor a medical device extending into a brain, the clamp having a bore therethrough for the passage of a medical device, and an inflatable member in the bore which when inflated can engage a medical device passing through the bore in the clamp, to releasably anchor the medical device.

11. The clamp of claim 10 wherein the clamp is shaped to abut substantially the entire circumference of the skull bore, and the clamp bore extends through the clamp and is itself surrounded by the clamp.

12. An intracranial bolt for installation in an opening in a skull to provide access to a brain for a medical device, the bolt having a bore therethrough for the passage of a medical device, and an inflatable member, in the bore, which when inflated can engage a medical device passing through the bore, to releasably anchor the medical device.

13. The intracranial bolt of claim 12 wherein the bolt is shaped to abut substantially the entire circumference of the opening, and the bore extends through the bolt and is itself surrounded by the bolt.

14. The intracranial bolt according to claim 12 wherein the inflatable member extends around the circumference of the bore, and upon inflation expands radially inwardly into the bore.

15. The intracranial bolt according to claim 14 wherein the inflatable member comprises a cylinder of flexible sheet material inside the bore, the cylinder having first and second ends, and being secured to the wall of the bore at the first and second ends, the cylinder and wall of the bore defining an annular pocket therebetween, the cylinder expanding radially inwardly into the bore upon the introduction of fluid into the pocket.

16. The intracranial bolt according to claim 12 wherein the inflatable member comprises an annular balloon in the bore through which the medical device extends.

17. The intracranial bolt according to claim 10 wherein the inflatable member is formed by a wall of the bore and a panel of flexible material extending around the circumference of the bore.

18. An intracranial bolt for installation in an opening in a skull to provide access to a brain for a medical device, the bolt having a distal portion adapted to be secured in the opening of the skull, and a proximal portion adapted to project from the skull when the bolt is installed in the opening, and a bore extending between the proximal and distal sections, the proximal portion adapted to sealingly receive a cap for closing the proximal end of the bore.

19. The intracranial bolt of claim 18 wherein the bolt is shaped to abut substantially the entire circumference of the opening, and the bore extends through the bolt and is itself surrounded by the bolt.

20. The intracranial bolt according to claim 18 further comprising an inflatable member, in the bore, which when inflated, expands in the bore to engage a medical device passing through the bore.

21. The intracranial bolt according to claim 20 wherein the inflatable member comprises a panel of flexible material secured over a wall of the bore to form a pocket therebetween, and a passage through the bolt communicating with the pocket for introducing fluid into the pocket to urge the panel away from the wall and into the pocket.

22. The intracranial bolt according to claim 21 wherein the panel extends circumferentially around the bore.

23. A method of performing a medical procedure on the brain comprising:
    forming an opening in the skull;
    installing an intracranial bolt in the opening in the skull, the intracranial bolt having a distal portion adapted to be secured in the opening in the skull, a proximal portion adapted to project from the skull when the bolt is installed in the opening, and a bore extending between the proximal and distal sections for providing access to the brain through the bolt;

securing a cap on the proximal end of the bolt; and removing the cap after installation of the bolt and inserting a medical device through the bore in the bolt to perform a medical procedure on the brain.

24. The method according to claim 23 wherein the step of inserting a medical device through the bore in the bolt comprises inserting a cannula through the bore and into the brain to provide a pathway; and further comprising the step of replacing the cap on the bolt after the installation of the cannula.

25. A method of placing and temporarily anchoring a medical device through a skull and into a brain, the method comprising:

forming an opening in the skull;

installing an intracranial bolt in the opening in the skull, the bolt having a bore therethrough for the passage of a medical device, and an inflatable member in the bore which when inflated engages a medical device in the bore;

inserting a medical device through the bore of the bolt and into the brain; and inflating the inflatable member to engage the device, and releasably anchor the device.

26. The method according to claim 25, wherein the bolt is adapted to mount a cap, and further comprising the step of securing a cap on the bolt after the medical device has been inserted into the bore.

27. The method according to claim 25 wherein the inflatable member comprises a panel of flexible sheet material secured over a portion of the wall of the bore to form a pocket between the panel and wall, and wherein the step of inflating the inflatable member comprises introducing fluid into the pocket to urge the flexible panel away from the wall and into the bore to engage the medical device in the bore.

28. The method according to claim 27 wherein the panel extends circumferentially around the wall of the bore.

\* \* \* \* \*